United States Patent [19]

Ohno et al.

[11] Patent Number: 5,028,633
[45] Date of Patent: Jul. 2, 1991

[54] EXCIPIENT FOR USE IN COMPRESSION MOLDING AND PROCESS OF PREPARATION

[75] Inventors: Shigeru Ohno, Tokyo; Masayuki Ikeda, Sakado, both of Japan

[73] Assignee: Freund Industrial Co., Ltd., Tokyo, Japan

[21] Appl. No.: 703,765

[22] Filed: Feb. 21, 1985

[51] Int. Cl.$^5$ .................................................. B29B 9/12
[52] U.S. Cl. ........................................ 514/778; 264/12; 264/13; 514/777; 514/781
[58] Field of Search .................... 264/13, 12; 514/777, 514/778, 781

[56] References Cited

U.S. PATENT DOCUMENTS

| | | | |
|---|---|---|---|
| 3,341,415 | 9/1967 | Scott | 264/13 |
| 3,639,169 | 2/1972 | Broeg et al. | 514/777 |
| 3,870,790 | 3/1975 | Lowey et al. | 514/777 |
| 3,962,384 | 6/1976 | Cannalonga et al. | 264/7 |
| 4,112,215 | 9/1978 | Boessler et al. | 264/13 |
| 4,159,346 | 6/1979 | Omura et al. | 514/778 |
| 4,517,179 | 5/1985 | Raghunathan | 514/249 |

FOREIGN PATENT DOCUMENTS

| | | | |
|---|---|---|---|
| 55-24136 | 2/1980 | Japan | 514/778 |
| 55-49905 | 12/1980 | Japan | 264/13 |

Primary Examiner—Mary Lynn Theisen
Attorney, Agent, or Firm—Kane, Dalsimer, Sullivan, Kurucz, Levy, Eisele & Richard

[57] ABSTRACT

A process for preparing a compression molding excipient comprises dispersing cellulose powder and hydroxypropyl starch powder in water or aqueous solutions of starch or hydroxypropyl starch and spray drying the dispersion. The excipients are useful for tablet moldings having optimum hardness and disintegration properties.

4 Claims, No Drawings

EXCIPIENT FOR USE IN COMPRESSION MOLDING AND PROCESS OF PREPARATION

BACKGROUND OF THE INVENTION

1. Field of the Invention

The invention relates to the compression molding of tablets and the like and more particularly relates to excipients for use in compression molding and a process for preparing the excipients.

2. Brief Description of the Prior Art

When powder or granules are molded by compression, there are instances where the main ingredients to be molded are too small in quantity to be molded, or where the main ingredients are difficult to mold by compression. In those cases, a method has often been used in which compression molding is conducted after mixing the main ingredient with an inert substance which has good moldability. This inert substance with the required moldability is called the excipient. This method is often carried out in the production of pharmaceuticals, veterinary drugs, agricultural chemicals, food products and cosmetics and some other chemicals. Lactose, microcrystalline cellulose powder and calcium hydrogen phosphate have been widely used as the excipient.

However, difficulties exist in using these substances. For example, lactose has advantages of low cost and chemical inertness and gives compression moldings of high hardness, but of no disintegrability. For pharmaceuticals, veterinary drugs and agricultural chemicals, it is necessary for the molding to disintegrate in a relatively short time in water or in digestive juice. The molds using lactose as the excipient, usually don't disintegrate or require a long time for disintegration and frequently cannot be put to practical use. In order to overcome this disadvantage, disintegrants, such as starch, calcium carboxymethylcellulose and low-substituted hydroxypropyl methylcellulose etc., must be added in appropriate proportions.

However, adding disintegrants is complicated, because a suitable combination has to be selected from a vast number of possible combinations of main ingredients plus excipients plus disintegrants in various rations. Conventionally, determination of the formulation including selection of the type and proportion of disintegrant has depended on many tests, conducted by trial and error technique. This is costly and inefficient.

Microcrystalline cellulose powder has excellent properties as an excipient because it is chemically inert, and able to give moldings of relatively high hardness and good disintegration time. However, it has poor flowability which causes difficult handling. It cannot be poured smoothly into the mold. Moreover, microcrystalline cellulose powder is expensive.

Calcium hydrogen phosphate produces moldings with high hardness but it is an ionic substance which cannot be regarded as chemically inert. This means that the range of applications employing it is limited. In addition to this disadvantage, it gives moldings of poor disintegrability. Hence it is inconvenient for use in industry.

The method of the invention provides a process for preparing an excipient which eradicates all of the above-mentioned difficulties. In accordance with this invention there is provided an excipient which will give rise to moldings with excellent disintegratability and high hardness, and which is physiologically harmless, chemically inert, highly flowable and of low cost.

SUMMARY OF THE INVENTION

The invention comprises a process for preparing an excipient for use in compression molding, which comprises; dispersing proportion of cellulose powder and hydroxypropyl starch powder in water or aqueous solutions of starch or hydroxypropyl starch so as to provide a weight ratio in the range of from 9:1 to 4:6; and spray drying the obtained dispersion.

DETAILED DESCRIPTION OF THE INVENTION

Essentially, the process of this invention comprises dispersing cellulose powder and hydroxypropyl starch powder in water or aqueous solutions of starch or hydroxypropyl starch at a weight ratio in the range of 9:1 to 4:6, and then spray drying the obtained dispersion. This process can be carried out readily on an industrial scale.

Hydroxypropyl starch powder used in the process of the invention is well known as a filler for pharmaceutical tablet molding. It gives moldings having disintegrability but low strength. Therefore, hydropropyl starch itself is inadequate as a molding excipient.

Cellulose powder used in the invention is well known as a filler in pharmaceutical table compression. It gives molds having strength.

The cellulose powder has one disadvantage in that it is lacking in flowability. It is difficult to mix with other ingredients and difficult to pour into a mold. This eliminates its use in high speed operations of continuous tablet compression processes.

In accordance to with the invention, hydroxypropyl starch and cellulose powder are combined to form a composite material, which unexpectedly is free flowing, giving moldings of high hardness and high disintegrability. It is of course, physiologically harmless, chemically inert and low production cost. It is useful in high-speed automatic tableting machine molding.

Because of all these characteristics, the excipients of the invention can be used as an excellent excipient for compression molding of active ingredients.

The hydroxypropyl starch powder used in this invention is advantageously the propylene glycol ether of starch containing hydroxypropoxyl groups within the range of 1-8% by weight. If the content exceeds 8% by weight, it forms a paste with presence of water, at room temperature, which makes it undesirable. The cellulose powder is advantageously the commercially available pulverized pulp of such particle sizes that 90% of particles pass through a 250-mesh screen or higher. Microcrystalline cellulose powder also may be used.

The first step in carrying out the process of this invention is to disperse the above-described hydroxypropyl starch and the cellulose powders in water.

These powders may be dispersed in the water by any order of mixing. If the two powders are dispersed independently in water, this can be followed by combining the two dispersions. Also, if these powders are formed first into a concentrated dispersion, they may be followed by dilution with water. The most appropriate range of concentration of the solid components in the dispersion is normally within the range of 10-30% for smooth supply of the dispersion to a spray dryer, but no particular limitations exist. In addition, the apparatus used for dispersion can be selected from generally known equipment such as paddle-type or turbine-type high speed agitators.

Heating is not required for preparation of the dispersion. It is only essential to maintain the temperature of the mixture of hydroxypropyl starch and water below its glue forming point. The temperature at which hydroxypropyl starch forms glue varies according to the content of hydroxypropyl groups. In general hydroxypropyl starch used herein forms a glue at about 50° C. Advantageously the temperature should not rise above 30° C.

It is desirable to conduct continuous agitation of the dispersion obtained as described above to prevent sedimentation of the solid powder components, because if the dispersion is left to stand for 48 hours or longer, the powder forms a sediment layer with strong dilatancy.

In the next step, the dispersion is spray dried. Both a spray drier mounted by the spray nozzle and one mounted by a high speed rotary disc may be employed. However, the latter is recommended as it can be used for dispersions with high solids content and the size of particles obtained is more suitable as an excipient. There is no particular limitation in the temperature of the air used for spray drying. A temperature up to the level of 400° C. at the spray drier inlet does not cause any problems. It is inevitably desirable to decrease the outlet temperature for heat energy economy in order to reduce production costs. To achieve this, a wellknown established technique involves controlling the outlet air temperature, by regulating the flow rate of the drying air.

Thus, the outlet temperature is advantageously controlled to 40° C.±5° C. Excessively high outlet temperature (over 100° C.) may cause discoloration.

As described above, in accordance with the process of this invention, an excipient may be easily obtained on an industrial scale, which has high flowability and imparts excellent hardness and disintegrability to compression molded products.

It is generally known that the addition of protective colloids to dispersions which have dilatancy will alleviate that condition and also impart thixotropy. It is also generally known that water-soluble high polymers are addable to an aqueous dispersion. The inventors, however, found that many water soluble polymers such as polyvinyl alcohol, water soluble cellulose derivatives (methylcellulose, hydroxyethyl cellulose, hydroxypropyl cellulose or combined derivatives thereof), hydroxypropyl starch or starch, could change the property of the dispersions of this invention from dilatancy to thixotropy. Polyvinyl alcohol and water soluble cellulose derivatives are well known as an excellent binder for molding and often used for binding purpose in wet granulation process to make hard and strong granules. Contrary to this generally known fact, when these substances are used in a dispersion to make it thixotropic according to this invention, the resulting excipients gives only very weak molds by compression. Only starch and hydroxypropyl starch gave excellent results.

This is an unusual phenomena. The reason is not well clarified. However, it is likely that the film strength of these polymers, polyvinyl alcohol and the water soluble cellulose derivatives, is extremely strong which imparts toughness to the particles obtained by spray drying, leading to the phenomenon of a repulsive force against compression during the compression molding operation. In contrast, starch and its derivatives, which are remarkably weaker than polyvinyl alcohol and the water soluble cellulose derivatives, in film strength, can be considered as substances that do not prevent the production of a molded product with high hardness, because this repulsive force does not act.

The starch used in this invention can be corn starch, potato starch or sweet potato starch. The hydroxypropyl starch having a hydroxypropoxyl group content within the range of 1% to 25% by weight, may be used. The amount of the starch or hydroxypropyl starch to be used with the water employed as the dispersion medium, is appropriate within the range of 0.5% to 5% by weight. This is because at concentrations below 0.5%, the dispersion lacks the capacity for conversion of dilatancy to thixotropy which means that the purpose of this invention cannot be achieved easily. In addition, at concentrations above 5%, the dispersion can adequately convert to thixotropy, but the dispersion's viscosity increases remarkable necessitating excessive power for agitation and transportation. Furthermore, atomization of the dispersion into fine droplets in the spray dryer becomes difficult, and with their adhesion to the wall of the dryer, considerable loss cannot be avoided. Dissolving starch or hydroxypropyl starch in water can be achieved readily by using a well-known procedure of adding these substances to water and heating to a temperature equal to or above its glue forming temperature while performing agitation.

An embodiment of this invention comprises using an aqueous solution of starch or hydroxypropyl starch instead of water in preparing the above-described dispersion. This changes the property of the dispersion from dilatancy to thixotropy which permits easy agitation, leading to stabilization of the dispersion and good effect on the product.

The cellulose and hydroxypropyl starch powder are dispersed in the aqueous solution of starch or hydroxypropyl starch which has been obtained using this process, and the dispersion can be conducted in the same way as that described above for the case where the medium is water only.

The spray drying of the dispersion so obtained can also be performed in exactly the same way as that described for the dispersion liquid where water only is used as the medium. Naturally, sedimentation of the starch and hydroxypropyl starch powder in the dispersion is remarkably slower compared with that where water only is used as the dispersion medium. In addition, this process has the advantage that dilatancy does not occur which means that prevention of sedimentation by means of very gentle agitation is possible.

The product mixture of cellulose and hydroxypropyl starch obtained completely overcomes the above-described disadvantage of poor flowability, while the excellent and advantageous properties of each component are enhanced. The mixture obtained is extremely useful as an excipient for automatic continuous compression molding as it has very good flowability.

The following Examples show the manner and process of making and using the invention and set forth the best most contemplated by the inventor for carrying out the invention, but are not to be construed as limiting.

Where given, tablet hardness was determined using a Schreuniger hardness tester. Tablet disintegration times were determined in water at 25° C. using the apparatus designated for that purpose in the Japanese Pharmacopolia, X.

The Angle of repose: Where reported, the angle of repose of a composition is determined by measurement of the angle made between the surface of the loose, granular or powdery composition and the horizontal after rotation for 2 minutes at 2 r.p.m. in the glass vessel of a Miwa's Rotary Cylinder Type Repose Angel Tester.

EXAMPLE 1

5.5 kgs of hydroxypropyl starch powder having 2.98% by weight of hydroxypropoxyl groups and a loss on drying of 13.8% (HPS-101 by Freund Industrial Co., Ltd.) and 5.5 kgs of cellulose powder (KC Floc W-300 by Sanyo Kokusaku Pulp Co., Ltd.; minimum 90% passes through a 300-mesh screen) are added in small portions to 28.5 kgs of water while vigorously agitating the mixture. An aqueous dispersion with a 25.2% solids content is obtained. The dispersion is spray dried to obtain a white, free flowing powder. Loss on drying of the product is 4.0%.

The condition settings for the rotary disc type spray dryer used are shown in Table 1, below.

TABLE 1

| Feed speed of dispersion | 16.7 kgs/hr. |
|---|---|
| Speed of disc rotation | 20,000 r.p.m. |
| Hot air flow rate | 5.0 Nm$^3$/min |
| Temperature of hot air inlet | 350° C. |
| Temperature of hot air outlet | 50° C. |
| Operation time | 2 hrs. 20 min. |
| Amount of powdered product obtained | 9.8 kgs |

The flowability of the powder obtained in this example is good. As criterion for this flowability evaluation, measurements of the angle of repose are made and compared to the angle of repose measured on the starting materials (hydroxypropyl starch and cellulose powder) and also compared with the angle of repose of a product obtained by simple mechanical mixing of the same hydroxypropyl starch and cellulose powder in the same proportions given above in this example (control).

The comparative test results are given in Table 2 below.

TABLE 2

| Test Material | Angle of Repose |
|---|---|
| Hydroxypropyl starch | 85°–90° |
| Cellulose powder | 75°–80° |
| Product of this invention (Example 1) | 35° |
| Mechanical mixture of hydroxypropyl starch and cellulose powder (control) | 75°–80° |

Where the angle of repose is less than 45° the material has very good flowability. Where the angle is between 45°–55°, the flowability of the powder is less satisfactory, while within the range of 55°–75°, flowability is almost lacking. At 75° or above, flowability is completely lacking.

Next the test materials described in Table 2, above, are molded by compression using a rotary tableting machine. The results are shown in Table 3, below.

TABLE 3

| Test Material | Molding Character | Hardness of the molded product | Disintegration time for the molded product |
|---|---|---|---|
| Hydroxypropyl starch | Smooth handling not possible. | — | — |
| Cellulose powder | Rough to mold. | Too weak for measurement. | — |
| Product of this invention (Example 1) | Molded well. | 8.1 kgs | 40 seconds |
| Mechanical mixture of hydroxypropyl starch and cellulose powder (control) | Rough to mold with yield of only 25%. | 4.2 kgs | 63 seconds |

The product of this invention prepared in Example 1 showed exceptionally good performance in every test item, as shown in Table 3, above.

EXAMPLE 2

0.5 kg of hydroxypropyl starch having 2.98% by weight of hydroxypropoxyl groups and a loss on drying of 13.8% (HPS-101 by Freund Industrial Co., Ltd.), is added to 24.5 kgs of water. The temperature of the mixture is raised to 85°–90° C. while agitating and maintained at that temperature for 5 minutes to produce a solution. A further 25 kgs of water is added and the resulting solution cooled to room temperature. As a result, 49.5 kgs of 0.87% hydroxypropyl starch solution is obtained. To 11.52 kgs of this solution there is added 2.24 kgs of hydroxypropyl starch having 2.98% by weight of hydroxypropoxyl groups and a loss on during of 13.8% (HPS-101 by Freund Industrial Co., Ltd.) and 2.24 kgs of powder pulp (KC Floc w-300 by Sanyo Kokusaku Pulp Manufacturing Co. Ltd.; minimum 90% passes through 300 mesh screen, loss on drying 5.0%).

The mixture is agitated to produce 16.0 kgs of a dispersion containing 26.0% solids. The dispersion is then spray dried under the same conditions given in Table 4, below, employing the rotary disc type of spray dryer used in Example 1, supra. The spray dried product is a free-flowing powder, showing a loss on drying of 4.8%.

TABLE 4

| Feed speed of dispersion | 21.4 kgs/hr. |
|---|---|
| Speed of disc rotation | 20,000 r.p.m. |
| Hot air flow rate | 5.8 Nm$^3$/min |
| Temperature of hot air inlet | 345° C. |
| Temperature of hot air outlet | 53° C. |
| Operation time | 40 minutes |
| Amount of powdered product obtained | 3.5 kgs |

The flowability of the powder obtained in this Example 2 is good. The angle of repose of the product is 33°. The powder product obtained and also the same powder mixed with lactose powder is molded by compression using a rotary type tableting machine. The table results obtained are shown in Table 5, below.

TABLE 5

| Test Material | Molding Character | Hardness of the molded product | Disintegration time for the molded product |
|---|---|---|---|
| Product of this example | Smoothly molded. | 8.0 kgs | 40 seconds |
| Mixture of the product of this example with lactose powder* (in the ratio of 1:1 | Rough to mold with yield of only 25% | 11.3 kgs | 55 seconds |

TABLE 5-continued

| Test Material | Molding Character | Hardness of the molded product | Disintegration time for the molded product |
|---|---|---|---|
| by weight). | | | |

*Lactose powder is produced by DMV of Holland; minimum of 95% passes through a 100-micron screen.

Both the product powder and the mixture of the product and lactose powder showed good tablet properties. The mixture with no-disintegrable lactose underwent rapid disintegration.

EXAMPLE 3

This Example is not an Example of the invention, but is made for comparative purposes.

The procedure of Example 2, supra., is repeated, except that a 0.3% aqueous solution of hydroxypropyl cellulose is used instead of the 0.87% aqueous solution of hydroxypropyl starch used in Example 2. A powder was produced, with an angle of repose of 37°. The product's flowability is good. However, when the powder is molded into tablets using a rotary tableting machine, the tablets obtained give a hardness of only 1.2 kg, indicating poor strength.

EXAMPLE 4

To 12.52 kgs of a 1.2% aqueous hydroxypropyl starch solution, there is added 1.34 kg of hydroxypropyl starch (having 5.88% by weight of hydroxypropoxyl groups; 11.5% loss on drying; HPS-101 by Freund Industrial Co., Ltd.) and 3.14 kgs of cellulose powder (KC-Floc W-250 by Sanyo Kokusaku Pulp Manufacturing Co., Ltd.; minimum 90% passes through 250 mesh screen, loss on drying 3.8%). The mixture is agitated to form a dispersion. The dispersion obtained is then spray dryed in a rotary disc spray dryer under the conditions shown in Table 6, below. A free-flowing powder is obtained, having a loss on drying of 3.8%.

TABLE 6

| Feed speed of dispersion | 21.4 kgs/hr. |
|---|---|
| Speed of disc rotation | 20,000 r.p.m. |
| Hot air flow rate | 5.8 Nm²/min |
| Temperature of hot air inlet | 348° C. |
| Temperature of hot air outlet | 51° C. |
| Operation time | 40 minutes |
| Amount of powdered product obtained | 2.6 kegs |

Both the powder obtained and a 1:1 by weight mixture of this powder with lactose powder (DMV, supra.) is molded by compression using a rotary tableting machine. Molding proceeds smoothly and the table results obtained are shown in Table 7, below.

TABLE 7

| Test Material | Table Hardness | Tablet Disintegration Time |
|---|---|---|
| Powder Product of this Example 4 | 8.2 kgs | 44 seconds |
| Mixture of the product | 12.1 kgs | 63 seconds |

TABLE 7-continued

| Test Material | Table Hardness | Tablet Disintegration Time |
|---|---|---|
| of this example with lactose powder (1:1) | | |

EXAMPLE 5

A 0.82% aqueous solution of corn starch is produced by dissolving corn starch in hot water to 12.50 kgs of this solution there is added 0.71 kg of hydroxypropyl starch, having 4.63% by weight of hydroxypropoxyl groups and a 12.4% loss on drying (HPS-101 by Freund Industrial Co., Ltd.), and 2.82 kgs of powder pulp (KC-Floc W-300 by Sanyo-Kokusaku Pulp Manufacturing Co., Ltd., minimum 90% passes through 300 mesh screen, 4.2% loss on drying) the mixture is agitated to form a dispersion. The dispersion thus prepared is spray dryed in a rotary disc type spray dryer under the conditions given in Table 8, blow. A free-flowing powder is obtained having a loss upon drying of 4.5%.

TABLE 8

| Feed speed of dispersion | 21.4 kgs/hr. |
|---|---|
| Speed of disc rotation | 20,000 r.p.m. |
| Hot air flow rate | 5.8 Nm³/min |
| Temperature of hot air inlet | 348° C. |
| Temperature of hot air outlet | 51° C. |
| Operation time | 40 minutes |
| Amount of powdered product obtained | 2.8 kgs |

The powder obtained has extremely good flowability with an angle of repose of 45°. When the powder is molded by compression using a rotary tableting machine, the molding is smooth and the table test results are given in Table 9, below.

TABLE 9

| Test Material | Table Hardness | Tablet Disintegration Time |
|---|---|---|
| Product of this Example 5 | 8.3 kgs | 40 seconds |

What is claimed is:

1. A process for preparing an excipient for use in compression molding, which comprises; dispersing proportions of particles of pulverized cellulose pulp and hydroxypropyl starch powder containing from 1 to 8% by weight hydroxypropyl groups and having an angle of repose of 55° and up, in water so as to provide a dispersion with a weight ratio in the range of from 9:1 to 4:6; and spray drying the obtained dispersion.

2. A process for preparing an excipient for use in compression molding, which comprises; dispersing particles of pulverized cellulose pulp and hydroxypropyl starch powder having 1 to 8% by weight hydroxypropyl groups and having an angle of repose of 55° and up, in a 0.1 to 5% aqueous solution selected from solutions of the group consisting of starch and hydroxypropyl starch solutions so as to provide a weight ratio of particles to powder in the range of from 9:1 to 4:6; and spray drying the obtained dispersion.

3. A product obtained by the process of claim 1.

4. A product obtained by the process of claim 2.

* * * * *